(12) United States Patent
Yang (10) Patent No.: US 10,857,292 B2
(45) Date of Patent: Dec. 8, 2020

(54) INTRAVENOUS DRIP MONITORING METHOD AND SYSTEM

(71) Applicants: Mikotek Information Inc., Taipei (TW); Ching-Wen Yang, Taipei (TW)

(72) Inventor: Ching-Wen Yang, Taipei (TW)

(73) Assignees: Mikotek Information Inc., Taipei (TW); Ching-Wen Yang, Taipei (TW)

( * ) Notice: Subject to any disclaimer, the term of this patent is extended or adjusted under 35 U.S.C. 154(b) by 361 days.

(21) Appl. No.: 16/045,774

(22) Filed: Jul. 26, 2018

(65) Prior Publication Data

US 2019/0030243 A1     Jan. 31, 2019

(30) Foreign Application Priority Data

Jul. 28, 2017   (TW) .............................. 106125600 A (51) Int. Cl.
  *A61M 5/168*   (2006.01)
  *G16H 20/17*   (2018.01)

(52) U.S. Cl.
  CPC ...... *A61M 5/16845* (2013.01); *A61M 5/1689* (2013.01); *A61M 5/16895* (2013.01); *G16H 20/17* (2018.01); *A61M 2205/18* (2013.01); *A61M 2205/50* (2013.01); *A61M 2205/505* (2013.01); *A61M 2205/70* (2013.01)

(58) Field of Classification Search
  CPC ............ A61M 5/1689; A61M 5/16845; A61M 5/16895; A61M 2205/18; A61M 2205/50; A61M 2205/505; A61M 2205/70; A61M 2205/3379; G16H 20/17; G01G 15/001; G01G 19/00
  See application file for complete search history.

(56) References Cited

U.S. PATENT DOCUMENTS

2011/0205074 A1   8/2011   Feng et al.

FOREIGN PATENT DOCUMENTS

| CN | 2309147 Y | 3/1999 |
| CN | 105536098 A | 5/2016 |
| JP | 02-182267 A | 7/1990 |
| JP | 11221276 A * | 8/1999 |
| JP | 4014275 B2 * | 11/2007 |

* cited by examiner

*Primary Examiner* — Manuel L Barbee
(74) *Attorney, Agent, or Firm* — CKC & Partners Co., LLC (57) ABSTRACT

An intravenous drip monitoring method is provided. (A) A monitoring initializing signal is received. (B) A loaded weight is measured to be assigned to be an initial weight and a current weight when the loaded weight is smaller than an empty weight in (C). (D) An alert weight is calculated such that the predetermined minimum alert weight is assigned to be the alert weight. (E) The loaded weight is measured and assigned to be the current weight. (F) When the current weight is not smaller than the alert weight, (E) is performed. (G) When the current weight is between the alert weight and the empty weight, an alert module generates an alert signal and (E) is performed. (H) When the current weight is smaller than the empty weight, a reset to zero and a zero offset calibration is performed on the weighting module and (C) is performed.

20 Claims, 5 Drawing Sheets

INTRAVENOUS DRIP MONITORING METHOD AND SYSTEM

RELATED APPLICATIONS

This application claims priority to Taiwan Application Serial Number 106125600, filed Jul. 28, 2017, which is herein incorporated by reference.

BACKGROUND

Field of Invention

The present invention relates to an intravenous drip monitoring technology. More particularly, the present invention relates to an intravenous drip monitoring method and system.

Description of Related Art

Medical infusion are mostly transferred to the blood of the patients by using gravity drip, in which a bag or a bottle of infusion is hung on a fixed stand such that the infusion are dripped to the patients through an infusion tube due to the gravity. Currently, the process of the dripping is still monitored by human. When the process is finished or is abnormal, an alert key is required to be manually pressed to inform the medical staffs to handle the condition. Besides, when an efficient monitoring method is absent, the workload of the medical staffs is increased.

Accordingly, what is needed is an intravenous drip monitoring method and an intravenous drip monitoring system to address the issues mentioned above.

SUMMARY

An aspect of the present invention is to provide an intravenous drip monitoring method. The intravenous drip monitoring method includes the steps outlined below. (A) A monitoring initializing signal is received. (B) A current loaded weight is measured by a weight-measuring module. (C) The loaded weight is assigned respectively as an initial weight and a current weight when the loaded weight is smaller than an empty weight. (D) An alert weight is calculated according to the current weight to determine whether the alert weight is larger than a predetermined minimum alert weight and to make the alert weight equal to the predetermined minimum alert weight when the alert weight is not larger than the predetermined minimum alert weight. (E) The current loaded weight is measured by the weight-measuring module and the loaded weight is assigned as the current weight. (F) A monitoring status is changed to when the current weight is not smaller than the alert weight to further perform the step (E). (G) An alert status is changed to when the current weight is smaller than the alert weight and is not smaller than the empty weight to control an alert module to generate an alert signal to further perform the step (E). (H) An empty status is changed to when the current weight is smaller than the empty weight to perform a reset to zero and a zero offset calibration on the weight-measuring module to further perform the step (C).

Another aspect of the present invention is to provide an intravenous drip monitoring system that includes a storage module, an operation interface, a weight-measuring module and a processing module. The storage module is configured to store an application program. The processing module is electrically coupled to the storage module, the operation interface and the weight-measuring module and is configured to access and execute the application program in the storage module to perform an intravenous drip monitoring method that includes the steps outlined below. (A) A monitoring initializing signal is received through the operation interface. (B) A current loaded weight is measured by the weight-measuring module. (C) The loaded weight is assigned respectively as an initial weight and a current weight when the loaded weight is smaller than an empty weight. (D) An alert weight is calculated based on the current weight to determine whether the alert weight is larger than a predetermined minimum alert weight and to make the alert weight equal to the predetermined minimum alert weight when the alert weight is not larger than the predetermined minimum alert weight. (E) The current loaded weight is measured by the weight-measuring module and the loaded weight is assigned as the current weight. (F) A monitoring status is changed to when the current weight is not smaller than the alert weight to further perform the step (E). (G) An alert status is changed to when the current weight is smaller than the alert weight and is not smaller than the empty weight to control an alert module to generate an alert signal to further perform the step (E). (H) An empty status is changed to when the current weight is smaller than the empty weight to perform a reset to zero and a zero offset calibration on the weight-measuring module to further perform the step (C).

These and other features, aspects, and advantages of the present invention will become better understood with reference to the following description and appended claims.

It is to be understood that both the foregoing general description and the following detailed description are by examples, and are intended to provide further explanation of the invention as claimed.

BRIEF DESCRIPTION OF THE DRAWINGS

The invention can be more fully understood by reading the following detailed description of the embodiment, with reference made to the accompanying drawings as follows.

DETAILED DESCRIPTION

In order to make the objects, technical solutions and advantages of the present disclosure apparent, diagrams in combination of examples are used to describe the present disclosure in further detail. It should be understood that the specific embodiments described herein are merely examples for explaining the present disclosure and are not intended to limit the present disclosure.

Figure 1:
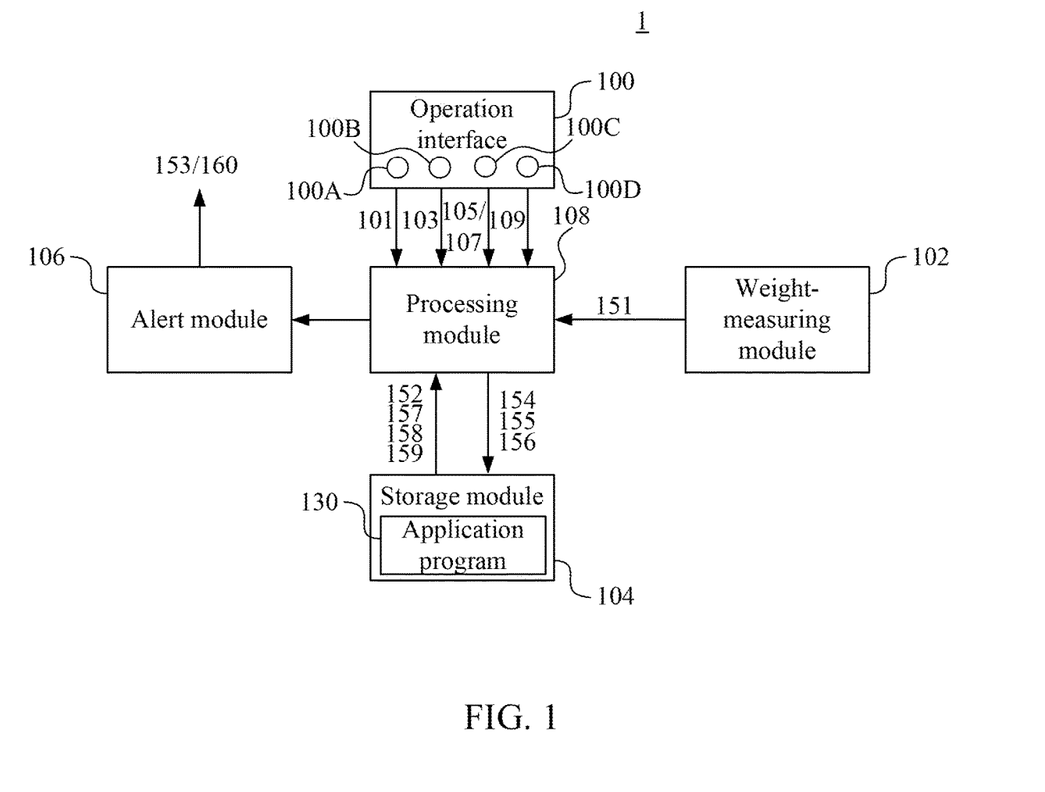
FIG. 1 is a block diagram of an intravenous drip monitoring system in an embodiment of the present invention.

Reference is now made to FIG. 1. FIG. 1 is a block diagram of an intravenous drip monitoring system 1 in an embodiment of the present invention. The intravenous drip monitoring system 1 includes an operation interface 100, a weight-measuring module 102, a storage module 104, an alert module 106 and a processing module 108.

The processing module 108 is electrically coupled to the operation interface 100, the weight-measuring module 102, the storage module 104 and the alert module 106.

The operation interface 100 may include such as, but not limited to a plurality of physical or virtual keys, such as but not limited to the keys 100A-100D. The user is able to press the keys 100A-100D to generate control signals such that the processing module 108 processes the control signals.

The weight-measuring module 102 is configured to perform weight measuring on an object to be measured, such as but not limited to an intravenous drip bag or an intravenous drip bottle. The processing module 102 can perform subsequent operations according to the weight measured by the weight-measuring module 102.

The storage module 104 may include a plurality of types of storage units, e.g. a register, a flash or a combination thereof, and is configured to store data. In an embodiment, the storage module 104 is configured to store an application program 130. The processing module 108 is configured to access the storage module 104 to store the processed data or retrieve data from the storage module 104.

The alert module 106 may include such as, but not limited to a buzzer, a light-emitting element or a combination thereof. The alert module 106 can generate alert message in the form of sound, flash light or a combination thereof based on the control of the processing module 108.

Figure 2:
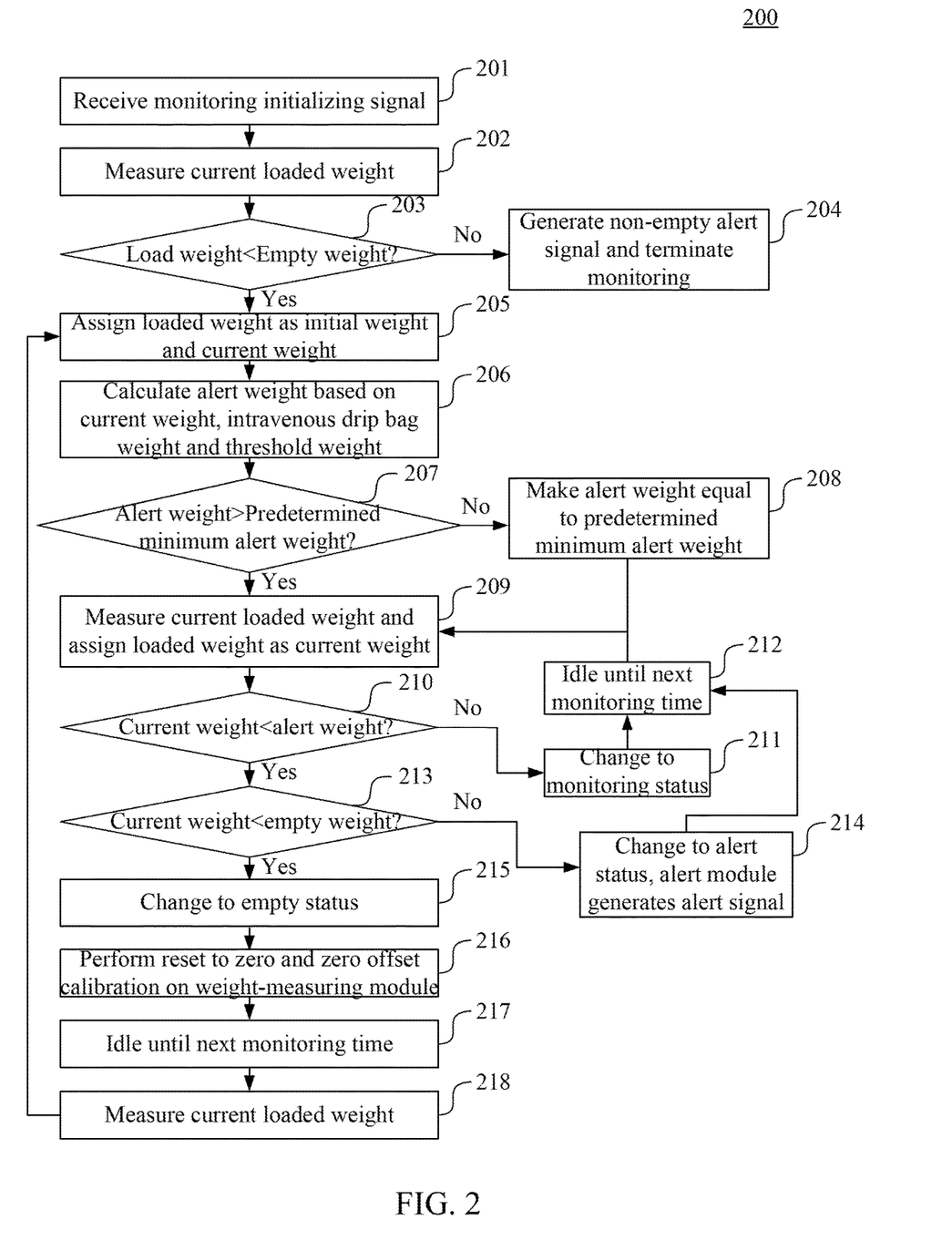
FIG. 2 is a flow chart of an intravenous drip monitoring method in an embodiment of the present invention.

The operation of the intravenous drip monitoring system 1 is described in detail in accompany with FIG. 1 and FIG. 2.

Reference is now made to FIG. 2. FIG. 2 is a flow chart of an intravenous drip monitoring method 200 in an embodiment of the present invention. The intravenous drip monitoring method 200 can be used in the intravenous drip monitoring system 1 in FIG. 1. The processing module 108 can retrieve and execute such as, but not limited to the application program 130 in the storage module 104 to perform the intravenous drip monitoring method 200. The intravenous drip monitoring method 200 includes the steps outlined below (The steps are not recited in the sequence in which the steps are performed. That is, unless the sequence of the steps is expressly indicated, the sequence of the steps is interchangeable, and all or part of the steps may be simultaneously, partially simultaneously, or sequentially performed).

In step 201, the processing module 108 receives a monitoring initializing signal 101 through the operation interface 100. In an embodiment, the monitoring initializing signal 101 can be generated by touching the physical or virtual keys of the operation interface 100, such as but not limited to the key 100A, by the user.

In step 202, a current loaded weight 151 is measured by the weight-measuring module 102.

In step 203, the processing module 108 determines whether the loaded weight 151 is smaller than an empty weight 152. In an embodiment, the value of the empty weight 152 can be stored in the storage module 104 and is retrieved by the processing module 108 to perform the determination described above.

In step 204, the processing module 108 determines that the weight-measuring module 102 is not under the empty status when the loaded weight 151 is not smaller than the empty weight 152. More specifically, there is still object hanging on the weight-measuring module 102, such as but not limited to an intravenous drip bag or an intravenous drip bottle, such that the loaded weight 151 is not smaller than the empty weight 152. As a result, the alert module 106 generates a non-empty alert signal 153 to terminate the monitoring.

When there is no object hanging on the weight-measuring module 102, the measured loaded weight may still not equal to zero due to such as, but not limited to the deformation of the weight-measuring module 102 generated due to the heavy object hanging thereon. As a result, when the loaded weight 151 is smaller than the empty weight 152, the processing module 108 determines that the weight-measuring module 102 is under the empty status.

In step 205, under the empty status, the processing module 108 assigns the loaded weight 151 respectively as an initial weight 154 and a current weight 155.

In an embodiment, the processing module 108 stores the values of the initial weight 154 and the current weight 155 in the storage module 104.

In step 206, the processing module 108 calculates an alert weight 156 based on the current weight 155. More specifically, in an embodiment, the processing module calculates the alert weight 156 according to the current weight 155, an intravenous drip bag weight 157 and a threshold weight 158.

In an embodiment, the threshold weight 158 is a threshold value that is set such that the alert can be generated before the infusion in the intravenous drip bag runs out. The intravenous drip bag weight 157 is the weight of the intravenous drip bag loaded by the weight-measuring module 102. In an embodiment, the values of the threshold weight 158 and the intravenous drip bag weight 157 can be stored in the storage module 104 and can be retrieved by the processing module 108 to perform calculation.

In step 207, the processing module 108 determines that whether the alert weight 156 is larger than a predetermined minimum alert weight 159.

In an embodiment, the predetermined minimum alert weight 159 is used to avoid the condition that the alert may not be generated forever due to the occurrence of unreasonable values of the alert weight 156. The predetermined minimum alert weight 159 can be stored in the storage module 104 and can be retrieved by the processing module 108 to perform the determination described above.

In step 208, when the alert weight 156 is not larger than the predetermined minimum alert weight 159, the processing module 108 makes the alert weight 156 equal to the predetermined minimum alert weight 159. When the alert weight 156 is larger than the predetermined minimum alert weight 159, the original value of the alert weight 156 is kept.

In an embodiment, the processing module 108 stores the value of the alert weight 156 determined in step 208 in the storage module 104.

In step 209, the weight-measuring module 102 measures the current loaded weight 151 and assigns the loaded weight 151 as the current weight 155. In an embodiment, the processing module 108 updates and stores the value of the current weight 155 in the storage module 104.

In step 210, the processing module 108 determines whether the current weight 155 is smaller than the alert weight 156.

In step 211, the processing module 108 further determines that a monitoring status is changed to when the current weight 155 is not smaller than the alert weight 156.

In an embodiment, the processing module 108 is configured to store a status value (not illustrated) in the storage module 104. By using different values, the status value is configured to represent different statuses of the intravenous drip monitoring system 1. For example, the processing module 108 can store such as, but not limited to the status value "0" to represent the monitoring status.

In an embodiment, the flow can selectively performs step 212, in which the processing module 108 idles until next monitoring time having the length of such as, but not limited to 30 seconds to go back to step 209 to further perform monitoring.

In step 213, the processing module 108 further determines whether the current weight 155 is smaller than the empty weight 152 when the processing module 108 determines that the current weight 155 is smaller than the alert weight 156 in the 210.

In step 214, when the processing module 108 determines that the current weight 155 is not smaller than the empty weight 152, the processing module 108 further determines that an alert status is changed to to control the alert module 106 to generate an alert signal 160.

In an embodiment, the processing module 108 can such as, but not limited to the status value "1" to represent the alert status.

In an embodiment, the flow can selectively performs step 212, in which the processing module 108 idles until next monitoring time having the length of such as, but not limited to 30 seconds to go back to step 209 to further perform monitoring.

In step 215, the processing module 108 further determines that an empty status is changed to when the processing module 108 determines that the current weight 155 is smaller than the empty weight 152 in step 213.

In an embodiment, the processing module 108 can such as, but not limited to the status value "2" to represent the empty status.

In step 216, the processing module 108 performs a reset to zero and a zero offset calibration on the weight-measuring module 102. In an embodiment, the reset to zero and the zero offset calibration allows the weight-measuring module 102 to use the initial weight 154 as the reference point. More specifically, the initial weight 154 is treated as 0 kilogram to accomplish the calibration.

In an embodiment, the flow can selectively performs step 217, in which the processing module 108 idles until next monitoring time having the length of such as, but not limited to 30 seconds to further perform monitoring.

In step 218, the measuring module 102 measures the current loaded weight 151. The flow further goes back to step 205 to keep performing the intravenous drip monitoring method 200.

FIG. 2 is used as the reference to describe the embodiment of the intravenous drip monitoring method 200 by using practical values in the following paragraphs. In an embodiment, values the empty weight 152, the intravenous drip bag weight 157, the threshold weight 158 and the minimum alert weight 159 are such as, but not limited to 30, 500, 30 and 100 kilograms respectively.

In step 201, when there is still no intravenous drip on the measuring module 102, the processing module 108 receives the monitoring initializing signal 101.

In step 202, the measuring module 102 measures the current loaded weight 151. In a embodiment, when there is no intravenous drip on the measuring module 102, the measured loaded weight 151 is 15 kilograms.

In step 203, the processing module 108 determines that the loaded weight 151 (15 kilograms) is smaller than the empty weight 152 (30 kilograms) and further determines that the measuring module 102 is under the empty status.

In step 205, the processing module 108 assigns the loaded weight 151 respectively as an initial weight 154 and a current weight 155.

In step 206, the processing module 108 calculates the alert weight 156 according to the current weight 155 (15 kilograms), the intravenous drip bag weight 157 (500 kilograms) and the threshold weight 158 (30 kilograms). As a result, the value of the alert weight 156 is 15−500+30=455 kilograms.

In step 207, since the calculated alert weight 156 is −455 kilograms, which is not larger than the predetermined minimum alert weight 159 that is 100 kilograms, the processing module 108 determines that the alert weight 156 is not larger than the predetermined minimum alert weight 159.

In step 208, the processing module 108 makes the alert weight 156 equal to the predetermined minimum alert weight 159 (100 kilograms).

In step 209, the measuring module 102 measures the current loaded weight 151 (which is still 15 kilograms), and the processing module 108 assigns the loaded weight 151 as the current weight 155.

In step 210, the processing module 108 determines that the current weight 155 (15 kilograms) is smaller than the alert weight 156 (100 kilograms).

In step 213, the processing module 108 determines that the current weight 155 (15 kilograms) is smaller than the empty weight 152 (30 kilograms).

In step 215, the processing module 108 determines that an empty status is changed to.

In step 216, the processing module 108 performs the reset to zero and the zero offset calibration on the weight-measuring module 102.

In step 217, the processing module 108 idles until next monitoring time.

In step 218, the measuring module 102 measures the current loaded weight 151. In an embodiment, when an intravenous drip having the infusion is loaded by the weight-measuring module 102, the weight-measuring module 102 measures such as, but not limited to 700 kilograms.

As a result, the flow goes back to step 205, the processing module 108 assigns the loaded weight 151 respectively as an initial weight 154 and a current weight 155.

In step 206, the processing module 108 further calculates the alert weight 156 according to the current weight 155 (700 kilograms), the intravenous drip bag weight 157 (500 kilograms) and the threshold weight 158 (30 kilograms). As a result, the value of the alert weight 156 is 700−500+30=230 kilograms.

In step 207, since the calculated alert weight 156 is 230 kilograms, which is larger than the predetermined minimum alert weight 159 that is 100 kilograms, the processing module 108 determines that the alert weight 156 is larger than the predetermined minimum alert weight 159.

In step 209, the measuring module 102 measures the current loaded weight 151 (which is still 700 kilograms), and the processing module 108 assigns the loaded weight 151 as the current weight 155.

In step 210, the processing module 108 determines that the current weight 155 (700 kilograms) is not smaller that the alert weight 156 (230 kilograms).

In step 211, the processing module 108 determines that a monitoring status is changed to.

In step 212, the processing module 108 idles until next monitoring time. The flow goes back to step 209, and the processing module 108 keeps determining whether the current weight 155 is smaller than the alert weight 156 in step 210.

Since the intravenous drip keeps outputting the infusion stored therein, the weight of the intravenous drip gradually decreases such that the loaded weight 151 measured by the weight-measuring module 102 decreases.

When the loaded weight 151 decreases such that the processing module 108 determines that the current weight 155 is smaller than the alert weight 156 in step 210, the flow goes to step 213, in which the processing module 108 determines whether the current weight 155 is smaller than the empty weight 152. Under such a condition, due to the existence of the weight of the intravenous drip bag, the processing module 108 keeps determining that the current weight 155 is not smaller than the empty weight 152.

In step 214, the processing module 108 determines that the alert status is changed to to control the alert module 106 to generate the alert signal 160.

In step 212, the processing module 108 idles until next monitoring time. The flow goes back to step 209 to keep performing step 210 and step 213 to determine that the current weight 155 is smaller than the alert weight 156 and is not smaller than the empty weight 152 until the flow to terminate the monitoring is activated or the intravenous drip bag is removed such that step 215 is performed.

As a result, the intravenous drip system 1 and the intravenous drip method 200 of the present invention is able to monitor the weight of the intravenous drip bag that includes infusion such that an alert is generated when the weight of the intravenous drip bag having the infusion decreases to be smaller than the alert weight due to the output of the infusion. Further, by keeping performing the reset to zero and the zero offset calibration on the weight-measuring module 102 under the empty status, the offset generated due to the deformation of the weight-measuring module 102 caused by the intravenous drip bag loaded by the weight-measuring module 102 for a long time can be avoided. Further, the offset generated due to the deformation of the weight-measuring module 102 caused by the removal of the intravenous drip bag can be avoided as well.

Figure 3:
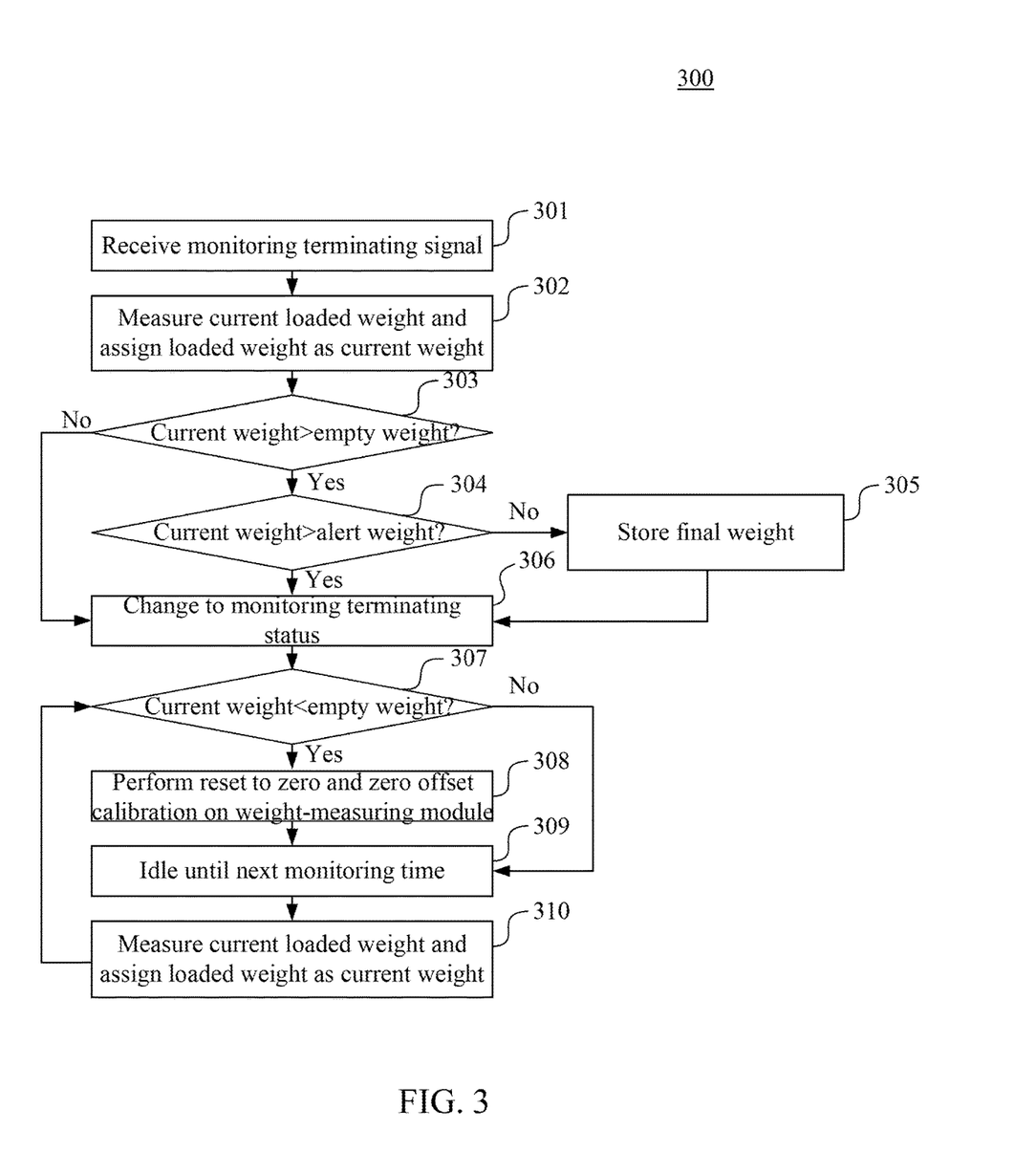
FIG. 3 is a flow chart of an intravenous drip monitoring method in an embodiment of the present invention.

Reference is now made to FIG. 1 and FIG. 3 at the same time. FIG. 3 is a flow chart of an intravenous drip method 300 in an embodiment of the present invention. The intravenous drip method 300 can be used in the intravenous drip system 1 in FIG. 1 and can be performed by the processing module 108 by retrieving and executing the application program 130 stored in the storage module 104.

In the present embodiment, the intravenous drip method 300 is used in the flow of the intravenous drip method 200 to terminate the monitoring according to the control of the operation interface 100. The intravenous drip method 300 includes the steps outlined below (The steps are not recited in the sequence in which the steps are performed. That is, unless the sequence of the steps is expressly indicated, the sequence of the steps is interchangeable, and all or part of the steps may be simultaneously, partially simultaneously, or sequentially performed).

In step 301, the processing module 108 receives the monitoring terminating signal 103 through the operation interface 100. In an embodiment, the monitoring terminating signal 103 can be generated by touching the physical or virtual keys of the operation interface 100, such as but not limited to the key 1006, by the user.

In step 302, the measuring module 102 measures the current loaded weight 151, and assigns the loaded weight 151 as the current weight 155. In an embodiment, the processing module 108 updates and stores the value of the current weight 155 in the storage module 104.

In step 303, the processing module 108 determines whether the current weight 155 is larger than the empty weight 152.

In step 304, when the processing module 108 determines the current weight 155 is larger than the empty weight 152, the processing module 108 further determines whether the current weight 155 is larger than the alert weight 156.

In step 305, when the processing module 108 determines the current weight 155 is larger than the alert weight 156, the processing module 108 records and stores the current weight 155 as a final weight. In an embodiment, the final weight can be used to perform big data analysis.

In step 306, the processing module 108 determines that the monitoring terminating status is changed to after the final weight is stored in step 305, when the current weight 155 is determined to be larger than the alert weight 156 in step 304 or when the current weight 155 is determined to be larger than the empty weight 152 in step 303. In an embodiment, the processing module 108 can store such as, but not limited to the status value "3" to represent the monitoring terminating status.

In step 307, the processing module 108 determines whether the current weight 155 is smaller than the empty weight 152.

In step 308, when the processing module 108 determines that the current weight 155 is smaller than the empty weight 152 in step 307, the processing module further determines that the empty status is changed to to perform the reset to zero and the zero offset calibration on the weight-measuring module 102.

In step 309, the processing module 108 selectively idles until next monitoring time that is such as, but not limited to 30 seconds when the current weight 155 is determined to be not smaller than the empty weight 152 in step 307 or after the reset to zero and the zero offset calibration is performed on the weight-measuring module 102 in step 308.

In step 310, the measuring module 102 measures the current loaded weight 151, and assigns the loaded weight 151 as the current weight 155. The flow goes back to step 307 to keep performing determination.

Figure 4:
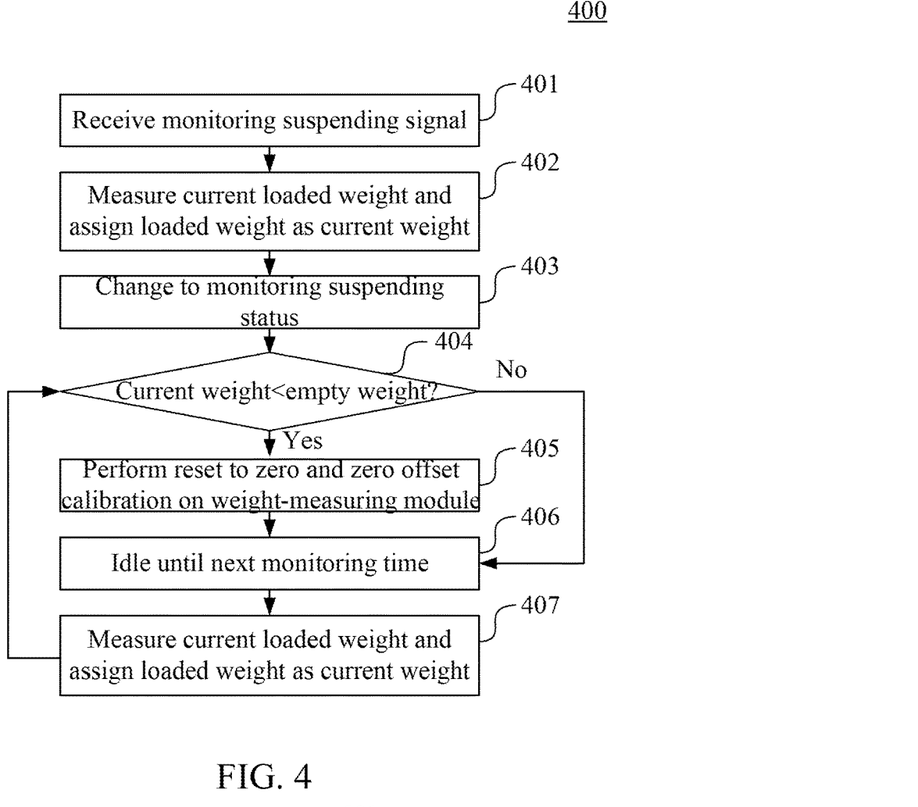
FIG. 4 is a flow chart of an intravenous drip monitoring method in an embodiment of the present invention.

Reference is now made to FIG. 1 and FIG. 4 at the same time. FIG. 4 is a flow chart of an intravenous drip method 400 in an embodiment of the present invention. The intravenous drip method 400 can be used in the intravenous drip system 1 in FIG. 1 and can be performed by the processing module 108 by retrieving and executing the application program 130 stored in the storage module 104.

In the present embodiment, the intravenous drip method 400 is used in the flow of the intravenous drip method 200 to suspend the monitoring according to the control of the operation interface 100. The intravenous drip method 400 includes the steps outlined below (The steps are not recited in the sequence in which the steps are performed. That is, unless the sequence of the steps is expressly indicated, the sequence of the steps is interchangeable, and all or part of the steps may be simultaneously, partially simultaneously, or sequentially performed).

In step 401, the processing module 108 receives the monitoring suspending signal 105 through the operation interface 100. In an embodiment, the monitoring suspending signal 105 can be generated by touching the physical or virtual keys of the operation interface 100, such as but not limited to the key 100C, by the user.

In step 402, the measuring module 102 measures the current loaded weight 151, and assigns the loaded weight 151 as the current weight 155. In an embodiment, the processing module 108 updates and stores the value of the current weight 155 in the storage module 104.

In step 403, the processing module 108 determines that the monitoring suspending status is changed to. In an embodiment, the processing module 108 can store such as, but not limited to the status value "4" to represent the monitoring suspending status.

In step 404, the processing module 108 determines whether the current weight 155 is smaller than the empty weight 152.

In step 405, the processing module 108 determines the empty status is changed to to perform the reset to zero and the zero offset calibration on the weight-measuring module 102 when the processing module 108 determines that the current weight 155 is smaller than the empty weight 152 in step 304.

In step 406, the processing module 108 selectively idles until next monitoring time that is such as, but not limited to 30 seconds when the current weight 155 is determined to be not smaller than the empty weight 152 in step 404 or after the reset to zero and the zero offset calibration is performed on the weight-measuring module 102 in step 405.

In step 407, the measuring module 102 measures the current loaded weight 151, and assigns the loaded weight 151 as the current weight 155. The flow goes back to step 404 to keep performing determination.

Figure 5:
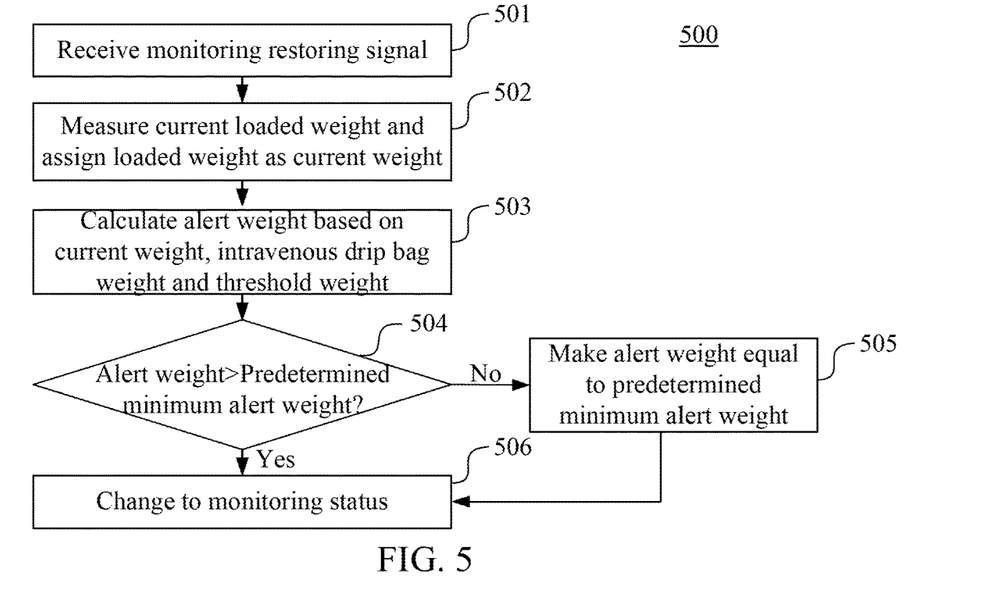
FIG. 5 is a flow chart of an intravenous drip monitoring method in an embodiment of the present invention.

Reference is now made to FIG. 1 and FIG. 5 at the same time. FIG. 5 is a flow chart of an intravenous drip method 500 in an embodiment of the present invention. The intravenous drip method 500 can be used in the intravenous drip system 1 in FIG. 1 and can be performed by the processing module 108 by retrieving and executing the application program 130 stored in the storage module 104.

In the present embodiment, the intravenous drip method 500 is used in the flow of the intravenous drip method 200 to restore the monitoring according to the control of the operation interface 100. The intravenous drip method 500 includes the steps outlined below (The steps are not recited in the sequence in which the steps are performed. That is, unless the sequence of the steps is expressly indicated, the sequence of the steps is interchangeable, and all or part of the steps may be simultaneously, partially simultaneously, or sequentially performed).

In step 501, the processing module 108 receives the monitoring restoring signal 107 through the operation interface 100. In an embodiment, the monitoring restoring signal 107 can be generated by touching the physical or virtual keys of the operation interface 100, such as but not limited to the key 100C, by the user.

In step 502, the measuring module 102 measures the current loaded weight 151, and assigns the loaded weight 151 as the current weight 155. In an embodiment, the processing module 108 updates and stores the value of the current weight 155 in the storage module 104.

In step 503, the processing module 108 calculates the alert weight 156 according to the current weight 155, the intravenous drip bag weight 157 and the threshold weight 158.

In step 504, the processing module 108 determines whether the alert weight 156 is larger than the predetermined minimum alert weight 159.

In step 505, when the alert weight 156 is not larger than the predetermined minimum alert weight 159, the processing module 108 makes the alert weight 156 equal to the predetermined minimum alert weight 159. When the alert weight 156 is larger than the predetermined minimum alert weight 159, the processing module 108 keeps the original value of the alert weight 156.

In an embodiment, the processing module 108 stores the determined value of the alert weight 156 in the storage module 104.

In step 506, the processing module 108 determines that the monitoring status is changed to. In an embodiment, the status of step 506 equals to the status of step 211 in FIG. 2. As a result, after step 506, the flow of FIG. 2 can be performed subsequently to keep performing monitoring.

As a result, the intravenous drip system 1 and the intravenous drip method 300-500 of the present invention can terminal, suspend and restore the monitoring flow in FIG. 2. Further, by keeping performing the reset to zero and the zero offset calibration on the weight-measuring module 102 under the empty status, the offset generated due to the deformation of the weight-measuring module 102 caused by the intravenous drip bag loaded by the weight-measuring module 102 for a long time can be avoided. Further, the offset generated due to the deformation of the weight-measuring module 102 caused by the removal of the intravenous drip bag can be avoided as well.

Figure 6:
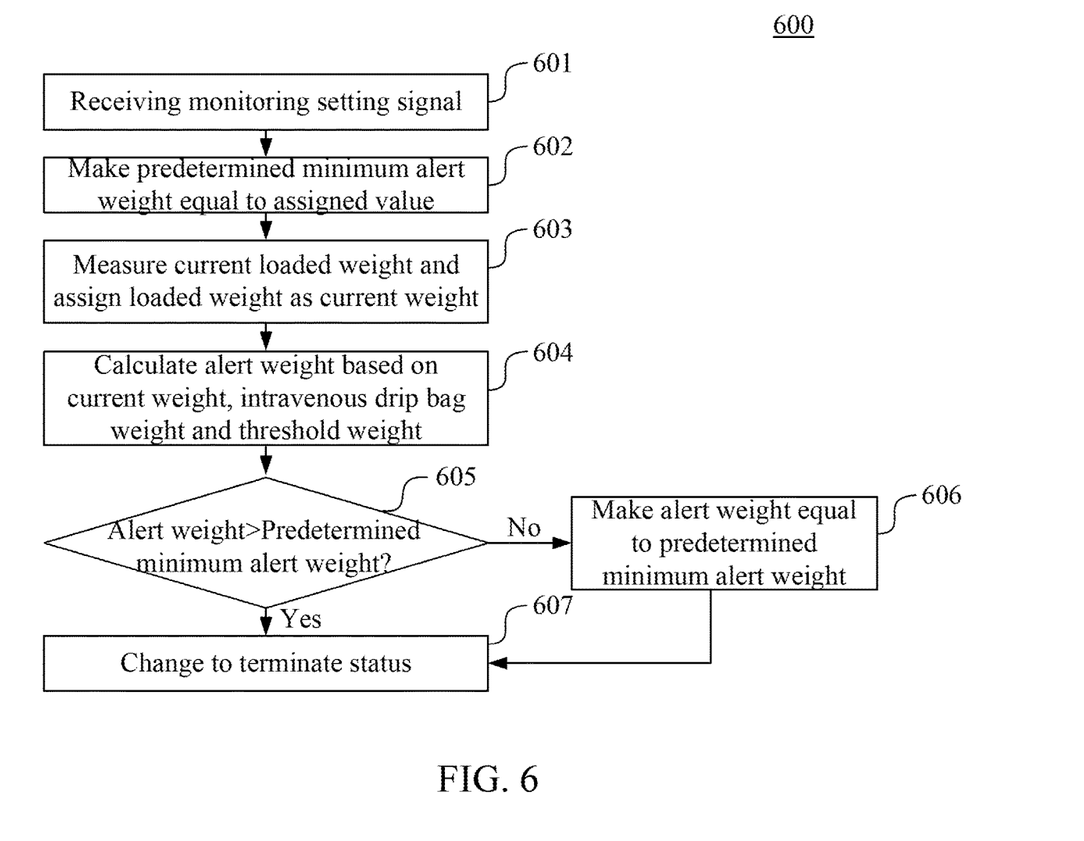
FIG. 6 is a flow chart of an intravenous drip monitoring method in an embodiment of the present invention.

Reference is now made to FIG. 1 and FIG. 6 at the same time. FIG. 6 is a flow chart of an intravenous drip method 600 in an embodiment of the present invention. The intravenous drip method 600 can be used in the intravenous drip system 1 in FIG. 1 and can be performed by the processing module 108 by retrieving and executing the application program 130 stored in the storage module 104.

In the present embodiment, the intravenous drip method 600 is used in the flow of the intravenous drip method 200 to set the predetermined minimum alert weight 159 according to the control of the operation interface 100. The intravenous drip method 600 includes the steps outlined below (The steps are not recited in the sequence in which the steps are performed. That is, unless the sequence of the steps is expressly indicated, the sequence of the steps is interchangeable, and all or part of the steps may be simultaneously, partially simultaneously, or sequentially performed).

In step 601, the processing module 108 receives the monitoring setting signal 109 through the operation interface 100. In an embodiment, the monitoring setting signal 109 can be generated by touching the physical or virtual keys of the operation interface 100, such as but not limited to the key 100D, by the user.

In step 602, the processing module 108 makes the predetermined minimum alert weight 159 equal to an assigned value.

In different embodiments, the processing module 108 can make the predetermined minimum alert weight 159 equal to the assigned value by using different methods. In an embodiment, the processing module 108 retrieves a value stored in the storage module 104 as the assigned value to modify the predetermined minimum alert weight 159. In another embodiment, the processing module 108 receives an input value from an input module (not illustrated) further included in the intravenous drip system 1 as the assigned value to modify the predetermined minimum alert weight 159.

In step 603, the measuring module 102 measures the current loaded weight 151, and assigns the loaded weight 151 as the current weight 155. In an embodiment, the processing module 108 updates and stores the value of the current weight 155 in the storage module 104.

In step 604, the processing module 108 calculates the alert weight 156 according to the current weight 155. More specifically, in an embodiment, the processing module 108 calculates the alert weight 156 according to the current weight 155, the intravenous drip bag weight 157 and the threshold weight 158.

In step 605, the processing module 108 determines whether the alert weight 156 is larger than the predetermined minimum alert weight 159 set in step 602.

In step 606, when the alert weight 156 is not larger than the predetermined minimum alert weight 159, the processing module 108 makes the alert weight 156 equal to the predetermined minimum alert weight 159. When the alert weight 156 is larger than the predetermined minimum alert weight 159, the processing module 108 keeps the original value of the alert weight 156.

In an embodiment, the processing module 108 stores the determined value of the alert weight 156 in the storage module 104.

In step 607, the setting is terminated.

It is appreciated that in an embodiment, when the processing module 108 uses the value stored in the storage module 104 as the assigned value to modify the predetermined minimum alert weight 159, the intravenous drip system 1 can dispose other keys on the operation interface 100 such that the processing module 108 accesses different values from the storage module 104 according to the monitoring setting signals generated by different keys and makes the predetermined minimum alert weight 159 equal to different assigned values. Different values can be applied according to different usage scenarios, such as but not limited to the usage of different sizes of the infusion tube adapted by the intravenous drip system 1.

For example, two different keys can be disposed at the operation interface 100 of the intravenous drip system 1 such that the processing module 108 can retrieve the values of 180 kilograms and 50 kilograms as the assigned values to correspond to a larger size of the infusion tube and a smaller size of the infusion tube. However, the present invention is not limited thereto.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims.

What is claimed is:

1. An intravenous drip monitoring method comprising:
   (A) receiving a monitoring initializing signal;
   (B) measuring a current loaded weight by a weight-measuring module;
   (C) assigning the loaded weight respectively as an initial weight and a current weight when the loaded weight is smaller than an empty weight;
   (D) calculating an alert weight based on the current weight to determine whether the alert weight is larger than a predetermined minimum alert weight and to make the alert weight equal to the predetermined minimum alert weight when the alert weight is not larger than the predetermined minimum alert weight;
   (E) measuring the current loaded weight by the weight-measuring module and assigning the loaded weight as the current weight;
   (F) changing to a monitoring status when the current weight is not smaller than the alert weight to further perform the step (E);
   (G) changing to an alert status when the current weight is smaller than the alert weight and is not smaller than the empty weight to control an alert module to generate an alert signal to further perform the step (E); and
   (H) changing to an empty status when the current weight is smaller than the empty weight to perform a reset to zero and a zero offset calibration on the weight-measuring module to further perform the step (C).

2. The intravenous drip monitoring method of claim 1, wherein the alert weight is a difference between the current weight and an intravenous drip bag weight and a sum of the difference and a threshold weight.

3. The intravenous drip monitoring method of claim 1, wherein between the step (F) and the step (E), between the step (G) to the step (E) and between the step (H) to the step (C), further comprising:
   idling until next monitoring time.

4. The intravenous drip monitoring method of claim 1, further comprising:
   (I1) receiving a monitoring terminating signal;
   (I2) measuring the current loaded weight by the weight-measuring module and assign the loaded weight as the current weight;
   (I3) changing to a monitoring terminating status when the current weight is larger than the alert weight and when the current weight is smaller than the empty weight; and
   (I4) recording the current weight and changing to the monitoring terminating status when the current weight is smaller than the alert weight and not smaller than the empty weight.

5. The intravenous drip monitoring method of claim 4, wherein after the step of changing to the monitoring terminating status, the wherein the intravenous drip monitoring method further comprises:
   (J1) determining that the weight-measuring module is under the empty status when the current weight is smaller than the empty weight to further perform the reset to zero and the zero offset calibration on the weight-measuring module; and
   (J2) measuring the current loaded weight by the weight-measuring module and assigning the loaded weight as the current weight after the reset to zero and the zero offset calibration are performed or when the current weight is larger than the empty weight to further perform the step (J1).

6. The intravenous drip monitoring method of claim 1, further comprising:
   (K1) receiving a monitoring suspending signal;
   (K2) measuring the current loaded weight by the weight-measuring module and changing to a monitoring suspending status;
   (K3) determining that the weight-measuring module is under the empty status when the current weight is smaller than the empty weight to further perform the reset to zero and the zero offset calibration on the weight-measuring module; and
   (K4) measuring the current loaded weight by the weight-measuring module and assigning the loaded weight as the current weight after the reset to zero and the zero offset calibration are performed or when the current weight is larger than the empty weight.

7. The intravenous drip monitoring method of claim 6, further comprising:
   (L1) receiving a monitoring restoring signal;
   (L2) measuring the current loaded weight by the weight-measuring module and assigning the loaded weight as the current weight;
   (L3) calculating the alert weight based on the current weight to determine whether the alert weight is larger than the predetermined minimum alert weight and to make the alert weight equal to the predetermined minimum alert weight when the alert weight is not larger than the predetermined minimum alert weight; and (L4) changing to a monitoring status to further perform the step (E).

8. The intravenous drip monitoring method of claim 1, wherein after the step (B), the intravenous drip monitoring method further comprises:
(M) controlling the alert module to generate a non-empty alert signal when the loaded weight is not smaller than the empty weight to terminate the monitoring.

9. The intravenous drip monitoring method of claim 1, further comprising:
(N1) receiving a monitoring setting signal;
(N2) making the predetermined minimum alert weight equal to an assigned value;
(N3) measuring the current loaded weight by the weight-measuring module and assigning the loaded weight as the current weight;
(N4) calculating the alert weight based on the current weight to determine whether the alert weight is larger than the predetermined minimum alert weight and to make the alert weight equal to the predetermined minimum alert weight when the alert weight is not larger than the predetermined minimum alert weight; and
(N5) finishing the setting.

10. An intravenous drip monitoring system comprising:
a storage module configured to store an application program;
an operation interface;
a weight-measuring module; and
a processing module electrically coupled to the storage module, the operation interface and the weight-measuring module and configured to access and execute the application program in the storage module to perform an intravenous drip monitoring method comprising:
(A) receiving a monitoring initializing signal through the operation interface;
(B) measuring a current loaded weight by the weight-measuring module;
(C) assigning the loaded weight respectively as an initial weight and a current weight when the loaded weight is smaller than an empty weight;
(D) calculating an alert weight based on the current weight to determine whether the alert weight is larger than a predetermined minimum alert weight and to make the alert weight equal to the predetermined minimum alert weight when the alert weight is not larger than the predetermined minimum alert weight;
(E) measuring the current loaded weight by the weight-measuring module and assigning the loaded weight as the current weight;
(F) changing to a monitoring status when the current weight is not smaller than the alert weight to further perform the step (E);
(G) changing to an alert status when the current weight is smaller than the alert weight and is not smaller than the empty weight to control an alert module to generate an alert signal to further perform the step (E); and
(H) changing to an empty status when the current weight is smaller than the empty weight to perform a reset to zero and a zero offset calibration on the weight-measuring module to further perform the step (C).

11. The intravenous drip monitoring system of claim 10, wherein the alert weight is a difference between the current weight and an intravenous drip bag weight and a sum of the difference and a threshold weight.

12. The intravenous drip monitoring system of claim 10, wherein between the step (F) and the step (E), between the step (G) to the step (E) and between the step (H) to the step (C), the processing module is further configured to idle until next monitoring time.

13. The intravenous drip monitoring system of claim 10, wherein the intravenous drip monitoring method executed by the processing module further comprising:
(I1) receiving a monitoring terminating signal through the operation interface;
(I2) measuring the current loaded weight by the weight-measuring module and assign the loaded weight as the current weight;
(I3) changing to a monitoring terminating status when the current weight is larger than the alert weight and when the current weight is smaller than the empty weight; and
(I4) recording the current weight and changing to the monitoring terminating status when the current weight is smaller than the alert weight and not smaller than the empty weight.

14. The intravenous drip monitoring system of claim 13, wherein after the step of changing to the monitoring terminating status, the intravenous drip monitoring method executed by the processing module further comprises:
(J1) determining that the weight-measuring module is under the empty status when the current weight is smaller than the empty weight to further perform the reset to zero and the zero offset calibration on the weight-measuring module; and
(J2) measuring the current loaded weight by the weight-measuring module and assigning the loaded weight as the current weight after the reset to zero and the zero offset calibration are performed or when the current weight is larger than the empty weight to further perform the step (J1).

15. The intravenous drip monitoring system of claim 10, wherein the intravenous drip monitoring method executed by the processing module further comprises:
(K1) receiving a monitoring suspending signal;
(K2) measuring the current loaded weight by the weight-measuring module and changing to a monitoring suspending status;
(K3) determining that the weight-measuring module is under the empty status when the current weight is smaller than the empty weight to further perform the reset to zero and the zero offset calibration on the weight-measuring module; and
(K4) measuring the current loaded weight by the weight-measuring module and assigning the loaded weight as the current weight after the reset to zero and the zero offset calibration are performed or when the current weight is larger than the empty weight.

16. The intravenous drip monitoring system of claim 15, wherein the intravenous drip monitoring method executed by the processing module further comprises:
(L1) receiving a monitoring restoring signal;
(L2) measuring the current loaded weight by the weight-measuring module and assigning the loaded weight as the current weight;
(L3) calculating the alert weight based on the current weight to determine whether the alert weight is larger than the predetermined minimum alert weight and to make the alert weight equal to the predetermined minimum alert weight when the alert weight is not larger than the predetermined minimum alert weight; and (L4) changing to a monitoring status to further perform the step (E).

17. The intravenous drip monitoring system of claim 10, wherein after the step (B), wherein the intravenous drip monitoring method executed by the processing module further comprises:

(M) controlling the alert module to generate a non-empty alert signal when the loaded weight is not smaller than the empty weight to terminate the monitoring.

18. The intravenous drip monitoring system of claim 10, wherein the processing module is further configured to store the initial weight, the current weight, the alert weight and the predetermined minimum alert weight in the storage module.

19. The intravenous drip monitoring system of claim 18, wherein the processing module is further configured to store a status value in the storage module, in which the status value represents the monitoring status, the empty status, the alert status, a monitoring terminating status and a monitoring suspending status.

20. The intravenous drip monitoring system of claim 10, wherein the intravenous drip monitoring method executed by the processing module further comprises:

(N1) receiving a monitoring setting signal;

(N2) making the predetermined minimum alert weight equal to an assigned value;

(N3) measuring the current loaded weight by the weight-measuring module and assigning the loaded weight as the current weight;

(N4) calculating the alert weight based on the current weight to determine whether the alert weight is larger than the predetermined minimum alert weight and to make the alert weight equal to the predetermined minimum alert weight when the alert weight is not larger than the predetermined minimum alert weight; and (N5) finishing the setting.

\* \* \* \* \*